US010463795B2

(12) United States Patent
Cappello et al.

(10) Patent No.: US 10,463,795 B2
(45) Date of Patent: Nov. 5, 2019

(54) NEEDLE-FREE INJECTION METHODS

(71) Applicant: PharmaJet, Inc., Golden, CO (US)

(72) Inventors: Chris Cappello, Broomfield, CO (US);
Matt Wixey, Rancho Santa Margarita, CA (US); John W. Bingham, Elizabeth, CO (US)

(73) Assignee: Pharmajet Inc., Golden, CO (US)

( * ) Notice: Subject to any disclaimer, the term of this patent is extended or adjusted under 35 U.S.C. 154(b) by 404 days.

(21) Appl. No.: 15/191,193

(22) Filed: Jun. 23, 2016

(65) Prior Publication Data
US 2016/0346475 A1 Dec. 1, 2016

Related U.S. Application Data

(62) Division of application No. 13/196,419, filed on Aug. 2, 2011, now Pat. No. 9,408,972.

(51) Int. Cl.
A61M 5/30 (2006.01)
A61M 5/20 (2006.01)

(52) U.S. Cl.
CPC ............ A61M 5/30 (2013.01); A61M 5/2033 (2013.01); A61M 2005/2013 (2013.01); A61M 2005/2026 (2013.01); A61M 2005/2073 (2013.01)

(58) Field of Classification Search
CPC .................. A61M 5/30; A61M 5/2033; A61M 2005/2013; A61M 2005/2026; A61M 2005/2073; A61M 5/326; A61M 5/20; A61M 5/3204; A61M 5/3202; A61M 5/31501; A61M 5/14546; A61M 5/31571; A61M 5/2053

USPC ................................................... 604/235, 68
See application file for complete search history.

(56) References Cited

U.S. PATENT DOCUMENTS

| 569,887 | A | | 10/1896 | Richardson | |
|---|---|---|---|---|---|
| 1,685,984 | A | * | 10/1928 | Cournand | A61M 5/24 604/235 |
| 1,757,809 | A | * | 5/1930 | Montuori | A61M 5/24 604/235 |

(Continued)

FOREIGN PATENT DOCUMENTS

| CA | 569887 | 2/1959 |
|---|---|---|
| EP | 1 093 826 | 4/2001 |

(Continued)

OTHER PUBLICATIONS

International Search Report dated Jun. 15, 2006, for PCT Patent Application No. PCT/US05/46041 filed on Dec. 20, 2005.

(Continued)

Primary Examiner — Manuel A Mendez
(74) Attorney, Agent, or Firm — Adsero IP

(57) ABSTRACT

Methods of operating needle-free injection device having an outer housing and an inner housing is disclosed. The inner housing is configured to receive a needle-free syringe in one end. In addition, the inner housing is movable within the outer housing between a syringe loading position and a firing position. The device may include an activation button operatively associated with the inner and outer housings and a housing lock engaged by the activation button to prohibit movement of the inner housing from the syringe loading position to the firing position when the activation button is activated with the inner housing in the syringe loading position.

18 Claims, 8 Drawing Sheets

(56) References Cited

U.S. PATENT DOCUMENTS

| | | |
|---|---|---|
| 2,547,099 A | 4/1951 | Smoot |
| 2,605,763 A | 8/1952 | Smoot |
| 2,635,601 A | 4/1953 | May |
| 2,645,223 A | 7/1953 | Lawshe et al. |
| 2,671,347 A | 3/1954 | Scherer |
| 2,687,724 A | 8/1954 | Ziherl et al. |
| 2,699,166 A | 1/1955 | Dickinson, Jr. et al. |
| 2,704,542 A | 3/1955 | Scherer |
| 2,704,543 A | 3/1955 | Scherer |
| 2,737,946 A | 3/1956 | Hein, Jr. |
| 2,764,977 A | 10/1956 | Ferguson |
| 2,800,903 A | 7/1957 | Smoot |
| RE24,419 E | 1/1958 | Ziherl et al. |
| 2,821,193 A | 1/1958 | Ziherl et al. |
| 2,821,981 A | 2/1958 | Ziherl et al. |
| 3,057,349 A | 10/1962 | Ismach |
| 3,115,133 A | 12/1963 | Morando |
| 3,131,692 A | 5/1964 | Love |
| 3,138,157 A | 6/1964 | Ziherl et al. |
| 3,202,151 A | 8/1965 | Kath |
| 3,292,621 A | 12/1966 | Banker |
| 3,292,622 A | 12/1966 | Banker |
| 3,335,722 A | 8/1967 | Lowry et al. |
| 3,424,154 A | 1/1969 | Kinsley |
| 3,461,867 A | 8/1969 | Zimmet et al. |
| 3,540,444 A | 11/1970 | Moreland |
| 3,688,765 A | 9/1972 | Gasaway |
| 3,695,266 A | 10/1972 | Lussier |
| 3,714,943 A | 2/1973 | Yanof et al. |
| 3,763,359 A | 10/1973 | Cho et al. |
| 3,763,859 A | 10/1973 | Yanof et al. |
| 3,788,315 A | 1/1974 | Laurens |
| 3,805,783 A | 4/1974 | Ismach |
| 3,815,594 A | 6/1974 | Doherty |
| 3,853,125 A | 12/1974 | Clark et al. |
| 3,859,996 A | 1/1975 | Mizzy et al. |
| 3,908,651 A | 9/1975 | Fudge |
| 3,933,155 A | 1/1976 | Johnston |
| 3,945,379 A | 3/1976 | Pritz et al. |
| 3,945,383 A | 3/1976 | Bennett et al. |
| 4,004,575 A | 1/1977 | Sarstedt |
| 4,031,889 A | 6/1977 | Pike |
| 4,059,107 A | 11/1977 | Iriguchi et al. |
| 4,089,334 A | 5/1978 | Schwebel et al. |
| 4,103,684 A | 8/1978 | Ismach |
| 4,124,024 A | 11/1978 | Schwebel |
| 4,128,098 A | 12/1978 | Bloom et al. |
| 4,301,795 A | 11/1981 | Zimmerman |
| 4,329,988 A | 5/1982 | Sarnoff et al. |
| 4,342,310 A | 8/1982 | Lindmayer et al. |
| 4,400,172 A | 8/1983 | Dettbarn et al. |
| 4,403,609 A | 9/1983 | Cohen |
| 4,403,989 A | 9/1983 | Christensen et al. |
| 4,421,508 A | 12/1983 | Cohen |
| 4,447,225 A | 5/1984 | Taff et al. |
| 4,475,905 A | 10/1984 | Himmelstrup |
| 4,507,113 A | 3/1985 | Dunlap |
| 4,518,385 A | 5/1985 | Lindmayer et al. |
| 4,592,742 A | 6/1986 | Landau |
| 4,596,556 A | 6/1986 | Morrow et al. |
| 4,680,027 A | 7/1987 | Parsons et al. |
| 5,106,371 A | 4/1992 | Zhao et al. |
| 5,211,628 A | 5/1993 | Marshall |
| 5,312,335 A | 5/1994 | McKinnon et al. |
| 5,312,348 A | 5/1994 | Sans |
| 5,397,313 A | 3/1995 | Gross |
| 5,499,972 A | 3/1996 | Parsons |
| 5,503,627 A | 4/1996 | McKinnon et al. |
| 5,527,284 A | 6/1996 | Ohnemus et al. |
| 5,531,705 A | 7/1996 | Alter et al. |
| 5,556,384 A | 9/1996 | da Encarnacao |
| 5,569,181 A | 10/1996 | Parsons |
| 5,569,189 A | 10/1996 | Parsons |
| 5,569,203 A | 10/1996 | Chen |
| 5,575,774 A | 11/1996 | Chen |
| 5,578,015 A | 11/1996 | Robb |
| 5,599,302 A | 2/1997 | Lilley et al. |
| 5,620,423 A | 4/1997 | Eykmann et al. |
| 5,649,912 A | 7/1997 | Peterson |
| 5,704,911 A | 1/1998 | Parsons |
| 5,782,802 A | 7/1998 | Landau |
| 5,865,795 A | 2/1999 | Schiff et al. |
| 5,891,086 A | 4/1999 | Weston |
| 5,899,879 A | 5/1999 | Umbauqh |
| 5,993,412 A | 11/1999 | Deily et al. |
| 6,053,895 A | 4/2000 | Kolberg et al. |
| 6,083,197 A | 7/2000 | Umbauqh |
| 6,123,684 A | 9/2000 | Deboer et al. |
| 6,224,577 B1 | 5/2001 | Dedola et al. |
| 6,319,224 B1 | 11/2001 | Stout et al. |
| 6,398,763 B1 | 6/2002 | Richardson et al. |
| 6,506,177 B2 | 1/2003 | Landau |
| 6,558,348 B2 | 5/2003 | Parsons |
| 6,673,035 B1 | 1/2004 | Rice et al. |
| 6,752,780 B2 | 6/2004 | Stout et al. |
| 6,942,638 B1 | 9/2005 | Quinn |
| 7,235,063 B2 | 6/2007 | D'Antonio et al. |
| 7,341,575 B2 | 3/2008 | Rice et al. |
| 7,442,182 B2 | 10/2008 | Landau et al. |
| 7,618,393 B2 | 11/2009 | Bingham et al. |
| 7,699,802 B2 | 4/2010 | Bingham et al. |
| 2001/0031945 A1 | 10/2001 | Haar et al. |
| 2001/0031956 A1 | 10/2001 | Drevik |
| 2002/0022806 A1 | 2/2002 | Witowski |
| 2002/0188251 A1 | 12/2002 | Staylor et al. |
| 2003/0065286 A1 | 4/2003 | Landau |
| 2003/0109846 A1 | 6/2003 | Zinger |
| 2003/0132547 A1 | 7/2003 | Heffernan et al. |
| 2003/0225368 A1 | 12/2003 | Landau et al. |
| 2004/0134563 A1 | 7/2004 | Rice et al. |
| 2004/0159364 A1 | 8/2004 | Landau et al. |
| 2006/0089593 A1 | 4/2006 | Landau et al. |
| 2006/0106362 A1 | 5/2006 | Pass et al. |
| 2007/0027428 A1 | 2/2007 | Binqham |
| 2007/0118094 A1 | 5/2007 | Bingham et al. |
| 2007/0167907 A1 | 7/2007 | Deslierres et al. |
| 2007/0191762 A1 | 8/2007 | Quinn |
| 2008/0015512 A1 | 1/2008 | D'Antonio et al. |
| 2008/0281261 A1 | 11/2008 | Steinway |
| 2009/0156992 A1 | 6/2009 | Landau |
| 2009/0247940 A1 | 10/2009 | Williamson et al. |
| 2010/0016374 A1 | 3/2010 | Landau |
| 2010/0076374 A1 | 3/2010 | Landau |
| 2010/0168662 A1 | 7/2010 | Bingham et al. |
| 2011/0257624 A1 | 10/2011 | Green |
| 2011/0319860 A1 | 12/2011 | Williamson et al. |

FOREIGN PATENT DOCUMENTS

| | | |
|---|---|---|
| KR | 10-2009-0051146 | 5/2009 |
| KR | 101052669 | 7/2011 |
| RU | 2192894 C2 | 11/2002 |
| RU | 2007111930 A | 10/2008 |
| WO | WO-95/03844 | 2/1995 |
| WO | WO-97/36783 | 10/1997 |
| WO | WO-02/05878 | 1/2002 |
| WO | WO-2004/041331 | 5/2004 |
| WO | WO-2006/009839 | 1/2006 |
| WO | WO-2006/106291 | 10/2006 |
| WO | WO-2006/118616 | 11/2006 |
| WO | WO-2007/146266 | 12/2007 |
| WO | WO-2008/063995 | 5/2008 |

OTHER PUBLICATIONS

International Search Report dated Oct. 11, 2007, for PCT Patent Application No. PCT/US2007/013744 filed on Jun. 12, 2007.
International Search Report dated Jul. 23, 2008, for PCT Patent Application No. PCT/US2007/84510 filed Nov. 13, 2007.
Supplementary Partial European Search Report dated Jul. 23, 2008, for EP Patent Application No. 05854705.0 filed Dec. 12, 2005.
International Search Report and Written Opinion dated Feb. 26, 2013 for International Application No. PCT/US2012/049312.

(56) References Cited

OTHER PUBLICATIONS

English translation of the Issue of Grant for corresponding Russian Application No. 2014103486 dated Jan. 26, 2015.
English translation of the Office Action for corresponding Korean Application No. 10-2014-7002855 dated Apr. 17, 2015.
Decision on Grant, RU-2015-119227, dated Nov. 6, 2018, 9 pages, English Translation provided.
Search Report RU-2015-119227, 4 pages, English Translation provided.

* cited by examiner

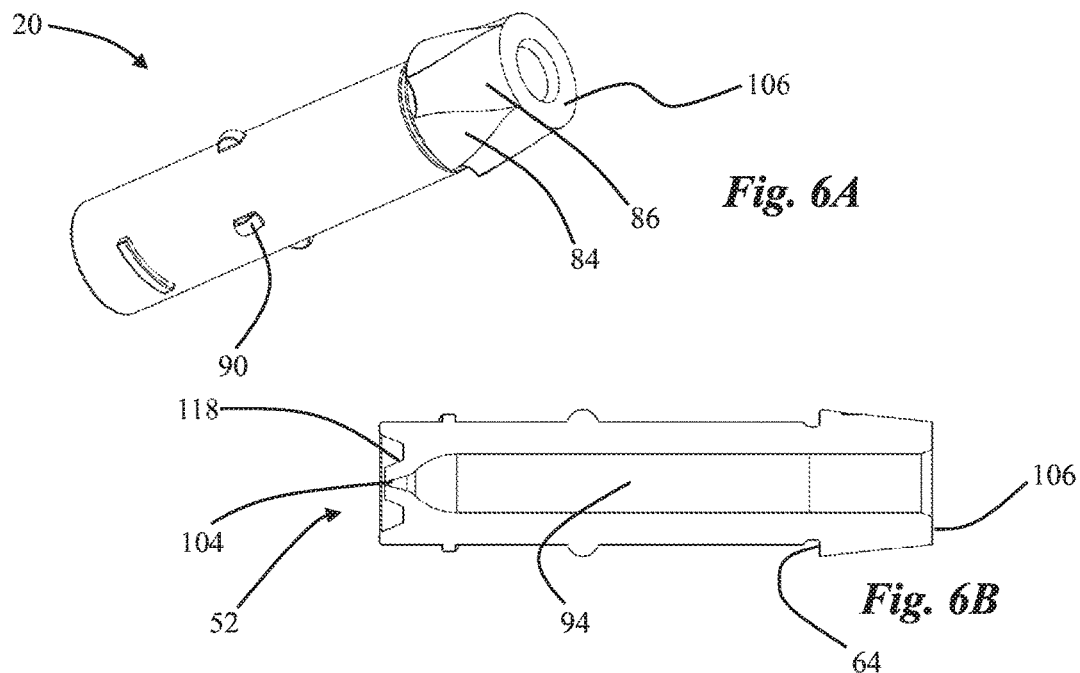
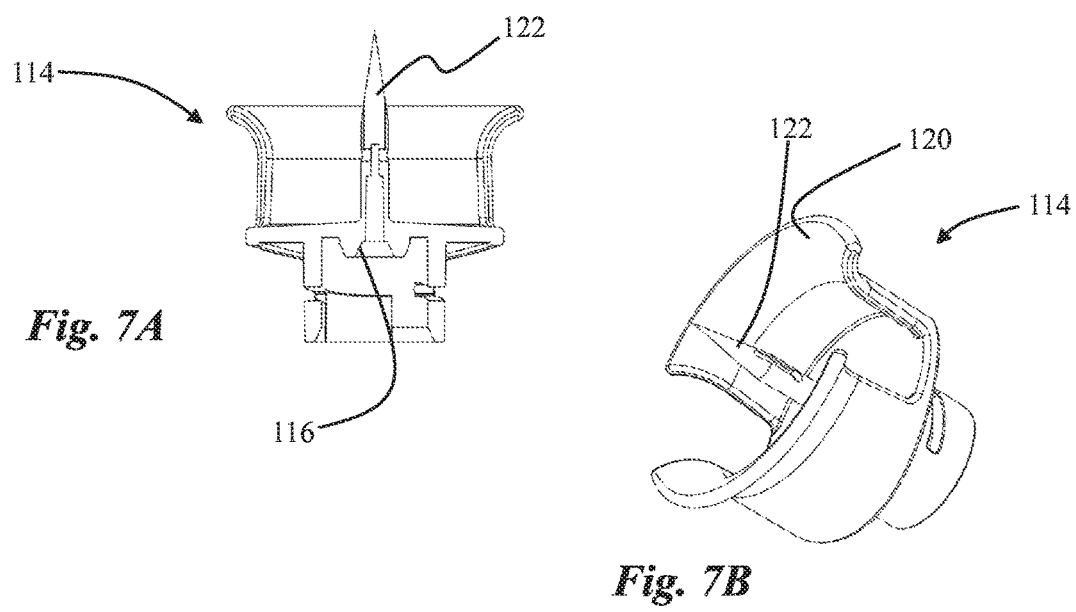

NEEDLE-FREE INJECTION METHODS

RELATED APPLICATIONS

This application is a divisional application of U.S. patent application Ser. No. 13/196,419 filed Aug. 2, 2011, entitled "Needle-Free Injection Device," which is incorporated herein in its entirety by reference for all matters disclosed therein.

TECHNICAL FIELD

The embodiments disclosed herein relate generally to needle-free injection devices and methods of injecting serums, medicine, inoculants or other injectable fluid into or through the skin of a human or animal.

BACKGROUND

The advantages of needle-free injection devices have been recognized for some time. Some of the advantages of needle-free devices and methods include the absence of a needle which can intimidate a patient and also present a hazard to healthcare workers. In addition, injection using a needle may increase the risk of cross-contamination between patients. Furthermore, with an injection device that employs a needle there is substantial risk of needle breakage in the tissue of a human or animal patient. The injection jet generated by a needle-free device is generally smaller in diameter than a hypodermic needle and thus in certain instances a needle-free injection is less painful than an injection provided by a hypodermic needle device.

Because of these and other advantages of needle-free injection many variations of pneumatic, electronic or spring activated needle-free injection devices have been designed to provide a single injection, or alternatively a series of injections to one or more patients. Most known needle-free injection devices operate by driving the injectable fluid through a fine nozzle with a powered piston to create a fine but high pressure jet of fluid that penetrates the skin. Needle free injection devices are not inherently risk free. For example, it is possible if precautions are not taken, to cause a laceration as opposed to a proper injection with a needle-free device. In addition, it is critical to design a needle-free device with safety features substantially minimizing the risk of inadvertent triggering or injection.

Thus, a great deal of attention has been given to the development of needle-free injection devices and methods which are safe, reliable and easy to use in the field. Needle-free technologies raise certain unique engineering challenges which are likely to be encountered when designing a suitable device. For example, conventional needled syringes are often inexpensive or disposable devices. Thus a large supply of pre-filled syringes can be prepared for large scale inoculation projects. On the other hand, needle-free devices are typically more expensive since these devices require a relatively sophisticated pneumatic, electronic or spring power source, energizing system and triggering system. Although a needle-free device can be designed to accept disposable (or recyclable) needle-free syringes, it can be difficult to quickly and accurately load a pre-filled needle-free syringe into an injection device, particularly without contaminating the injection nozzle. Similarly, it can be difficult to remove a spent needle-free syringe and replace same with an unused syringe quickly, efficiently and in a sterile manner. Thus, known needle-free injection devices can be difficult to use for large scale inoculation projects or in other situations where a significant number of injections are made to a relatively large group of patients.

Safety issues may involve the risk of accidental discharge of a needle-free device. Safety issue can become acute in association with devices that have exposed triggers or devices which include a ram or piston driving mechanism that can extend beyond the housing of the injector. The risk of using these types of devices is similar to the risks associated with the triggers on firearms. Thus, the inadvertent pressing of an exposed and armed trigger can cause the accidental or premature firing of the needle-free injection device.

One class of reliability issue with known needle-free injection devices involves difficulty delivering an entire preselected dosage of injectable liquid into the appropriate tissue of a patient. Dosage reliability issues have a broad spectrum of causes. One significant underlying cause is the difficulty encountered in the creation of a suitable jet or stream of fluid and introduction of this jet into or through the skin of a patient. Preferably, the jet will be a very fine jet that will impact a section of taught skin with much of the energy of the stream being used to penetrate the skin. The elasticity and permeability of a patient's skin can however vary with respect to other patients or across different locations on a patient's body. Another reliability issue concerns difficulty encountered efficiently and accurately pre-filling needle-free syringes to a selected dosage without significant waste of a potentially very limited supply of injectable fluid.

The embodiments disclosed herein are directed toward overcoming one or more of the problems discussed above.

SUMMARY OF THE EMBODIMENTS

One embodiment includes a needle-free injection device having an outer housing and an inner housing. The inner housing is configured to receive a needle-free syringe in one end. In addition, the inner housing is movable within the outer housing between a syringe loading position and a firing position. This embodiment also includes an activation button operatively associated with the inner and outer housings and a housing lock engaged by the activation button to prohibit movement of the inner housing from the syringe loading position to the firing position when the activation button is activated with the inner housing in the syringe loading position.

Generally, a syringe loading position is defined for any device as a configuration between inner and outer housings where syringe loading or syringe ejection is enabled and injection operations are substantially prohibited. In addition, for any device, a firing position is defined as a configuration between inner and outer housings where injection is enabled.

The housing lock of the above embodiment may be implemented with any suitable mechanism which serves to lock the inner housing in the syringe loading position with respect to the outer housing. For example, the housing lock can include an engagement surface on the activation button that mates with a corresponding recess on the inner housing.

In certain embodiments, the needle-free injection device further includes a powered hammer within the inner housing communicating with a plunger within a needle-free syringe. The hammer is released with a release mechanism to provide stored energy to the plunger to power an injection. Furthermore, the activation button is configured to only engage the release mechanism when the housing is in the firing position. Thus, in this embodiment, the activation button has at least two distinct functions. The activation button operates to lock the needle-free injection device in the syringe loading position when it is depressed or otherwise activated while in the syringe loading position and the same activation button operates to trigger the device and release stored energy to power the hammer, thus causing an injection, if the activation button is activated with the inner housing in the syringe loading position.

The release mechanism may be implemented with any suitable mechanism. For example, the release mechanism can comprise a lever associated with the activation button and a ball lock sleeve associated with the lever and the hammer such that articulation of the lever moves the ball lock sleeve thereby releasing the hammer. The hammer may be powered by any suitable pneumatic, spring, electronic or other power source.

In some embodiments, the needle-free injection device further includes a syringe mount to receive a needle-free syringe at one end of the inner housing. The syringe mount comprises an interlocking structure cooperating with the inner housing and outer housing to prevent the placement of a needle-free syringe into engagement with the syringe mount unless the inner housing is in the syringe loading position. The syringe mount and associated interlocking structure may be implemented with any suitable components, for example, the syringe mount and interlocking structure can comprise at least one rotating pawl providing for engagement with the needle-free syringe. A tab is provided toward the exterior of at least one pawl and a corresponding opening is provided through the inner housing. In addition, a corresponding space is provided within the outer housing such that the pawl can rotate to receive a syringe only if the opening through the inner housing is aligned with the space within the outer housing, for example, when the inner housing is in the syringe loading position. Alternatively, the pawl may be prohibited from rotating if the inner housing is not in a syringe loading position by tab interference with a corresponding portion of the outer housing.

The interlocking structure can also be configured to engage with the inner housing after a needle-free syringe is loaded such that force applied to a nozzle end of the needle-free syringe causes the inner housing to move from the syringe loading position toward the firing position. In addition, the interlocking structure can cooperate with the inner housing and outer housing to substantially prevent the removal of a needle-free syringe from engagement with the syringe mount unless the inner housing is in the syringe loading position. Furthermore, the interlocking structure can cooperate with the inner housing and outer housing to prevent the inner housing from being moved from the syringe loading position to the firing position if a syringe has been improperly loaded in the syringe mount.

Embodiments of the needle-free injection system further comprise an eject button associated with the syringe mount such that activation of the eject button causes the syringe mount to release a previously mounted needle-free syringe. Inadvertent syringe ejections are substantially prevented by providing an extension on the outer housing that at least partially shields the eject button when the inner housing is moved from the syringe loading position toward the firing position. In addition, the interlocking structure can prevent ejection unless the inner housing is in the syringe loading position. The system may optionally be provided with a syringe eject spring which provides sufficient force to completely eject a needle-free syringe away from any contact with the needle-free injection system upon activation of the eject button.

The needle free injection system may also comprise a needle-free syringe. The needle-free syringe may include at least two raised surfaces on the syringe body defining at least one orientation channel configured to mate with an orientation structure of the syringe mount. The syringe may further include a grip edge defined at least in part by the raised surfaces which engages the syringe mount when a needle-free syringe is mounted. The foregoing structures may be implemented to allow the mounting of a needle-free syringe without requiring rotation the syringe body or syringe mount to lock the syringe to the syringe mount. Furthermore, the foregoing structures and associated syringe mount and ejection structures may provide for the mounting, use and subsequent ejection of a needle-free syringe from the system without requiring that the syringe be touched or grasped by an operator's hand at any step of the process.

The foregoing embodiments of needle-free injection systems are described as including a multi-purpose activation button, housing lock and release mechanism subsystem, a syringe mount and interlocking structure subsystem and various features associated with a suitable needle-free syringe itself. Alternative device embodiments may include any combination of one or more of the foregoing subsystems or structures.

An alternative embodiment is a needle-free syringe comprising a syringe body having a nozzle at one end and a dose setting surface substantially opposite the nozzle. The needle-free syringe further includes a plunger body having a leading end, a seal and a hammer surface substantially opposite the leading end. In this configuration, the syringe body defines a dosage space within the syringe between the nozzle, interior syringe walls and the plunger seal. The dosage space has a select dosage volume when the plunger body is positioned within the syringe body such that the dose setting surface and hammer surface are coplanar. The selected dosage volume may be any suitable amount, for example, 0.5 ml.

The needle-free syringe system may optionally further include a handle substantially opposite the plunger body, a separable shaft between the plunger body and the handle, and a break line defined in the separable shaft. In this alternative, the break line defines the hammer surface on the plunger body. In addition, the handle may include a plunger positioning surface which cooperates with the hammer surface to position the plunger body in a needle-free syringe body such that the dose setting surface and hammer surface are coplanar. The plunger positioning surface may define a hole providing a clearance for any nub formed in the hammer surface upon separation of the plunger body from the handle at the break line.

The needle-free syringe system may further include a filling adapter. The filling adapter mates with the syringe body for filling operations. A fluid tight seal between the adapter and syringe body may be made by providing either the filling adapter or the syringe body with a female conical surface and providing the other of the syringe body or filling adapter with a corresponding male conical surface. The corresponding male and female conical surfaces form a fluid tight seal upon the attachment of the filling adapter to the nozzle end of the syringe body without the requirement of a separate compliant sealing member such as an o-ring.

The needle-free syringe system may also include a cap having an open ended cap body size to engage and protect the nozzle end of the syringe body and an annular flange at a closed end of the cap body which provides a stand surface having a diameter greater than the diameter of the open end of the cap body.

An alternative embodiment disclosed herein is a plunger and handle system for any needle-free syringe as described above. Another alternative embodiment is a filling adapter for any needle-free syringe system as described above.

Another embodiment is a method of operating a needle-free injector. The method includes providing a needle-free injection device according to one of the alternative embodiments described above. The method further includes activating the activation button to lock the inner housing in the syringe loading position and subsequently loading a needle-free syringe into the injector. An operator may then release the activation button and move the inner housing to the firing position by pressing the nozzle end of the needle-free syringe against the injection site with sufficient force. The injection may then be triggered by activating the activation button when the inner housing is fully in the firing position. Optionally, the method may include steps of loading and ejecting a needle free syringe from the device. Loading and ejection may occur without touching the syringe at any time.

An alternative embodiment is a method of filling a needle-free syringe including providing a syringe body having a nozzle at one end and a dose setting surface substantially opposite the nozzle and providing a plunger body in sealed engagement with an inner surface of the syringe body where the plunger body further comprises a hammer surface. The filling method further comprises positioning the hammer surface to be substantially coplanar with the dose setting surface.

An alternative method of filling a needle-free syringe may include providing a filling adapter with a filling needle in sealed fluid communication with the nozzle of the syringe body. The plunger system including a handle as described above may be placed into engagement with the syringe. The plunger body may then be moved forward to the nozzle end of the syringe body. The septum of storage vial of injectable fluid may be pierced with the filling needle. The plunger system is then withdrawn by the handle to a position where the break line is beyond the dose setting surface. The handle is then removed from the plunger body by separating the shaft at the break line. Next, the plunger body may be moved toward the nozzle by applying force against the hammer surface with a plunger positioning surface causing the hammer surface and dose setting surface to become coplanar. Alternatively, the dose may be set by using a surface within the device, for example the leading edge of the hammer, to cause the hammer surface to become coplanar with the dose setting surface. Throughout the dose setting operation the filling adapter and needle-free syringe remain in direct fluid communication with the storage vial of injectable fluid, thereby allowing the precise setting of an injection dosage without the waste of any substantial amount of injectable fluid.

BRIEF DESCRIPTION OF THE DRAWINGS

FIG. 2B shows the housing lock engaged.

FIG. 6A is a perspective view of a needle-free syringe.

FIG. 6B is a side cross sectional view of the needle-free syringe of FIG. 6A.

FIG. 7A is a side cross sectional view of a filling adapter.

FIG. 7B is a perspective view of the filling adapter of FIG. 7A.

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Figure 1:
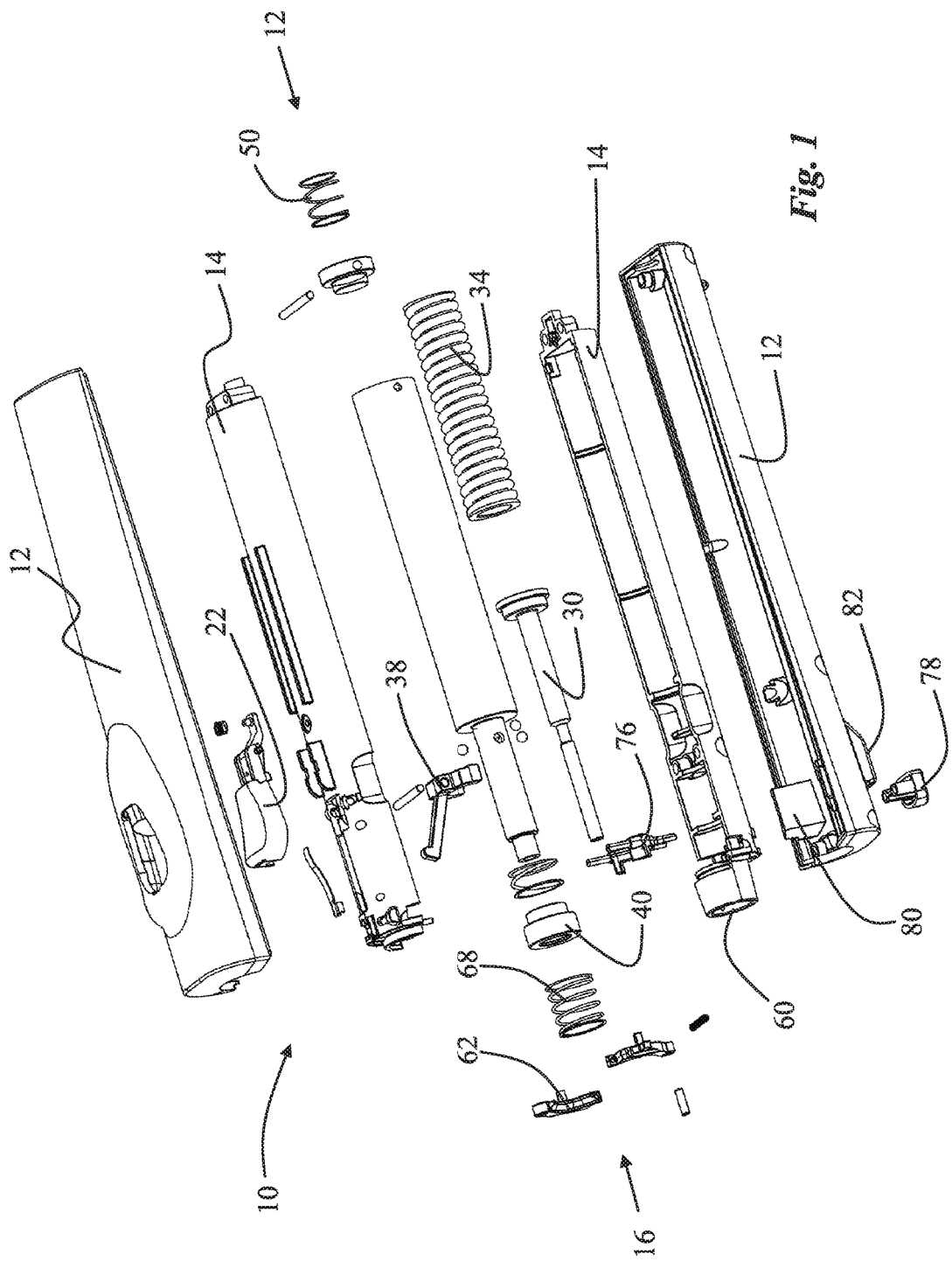
FIG. 1 is an exploded perspective view of a needle-free injection device.

FIG. 1 is an exploded perspective view of a needle-free injection device 10. The representative needle-free injection device 10 is further illustrated in the front elevation cross-section views of FIGS. 2A-2C and FIGS. 3A-3D. The views of FIGS. 2A-2C and FIGS. 3A-3D show the needle-free injection device 10 in various operational states as described in detail below. The needle-free injection device 10 includes an outer housing 12 and an inner housing 14. Although the outer housing 12 and inner housing 14 are shown separated into two halves in FIG. 1, this is a non-limiting fabrication choice. The housings may be fabricated from any suitable material in any number of sub-components provided the housings operate with respect to each other as described herein. In the embodiment illustrated in FIGS. 1-3, the outer housing 14 defines the exterior of a substantially cylindrical needle-free injection device which is conveniently sized for hand-held use. Both the device 10, outer housing 12 and inner housing 14 are described herein as having a leading end 16 which is defined as the injection end of the device generally associated with a needle-free syringe (see for example FIG. 2B). In addition, the device housings and syringe are described herein as having a trailing end 18 substantially opposite the leading end 16.

The foregoing position and shape descriptions are provided for convenience only and do not create any limiting configuration. For example, the needle-free injection device 10 is illustrated herein as being substantially cylindrical and sized for convenient hand-held use. The various features, elements, components and methods described herein are however applicable to other shapes, sizes and configurations of device. Thus, terms such as leading end and trailing end are provided merely to aid in the description of the representative embodiment and are not intended to limit the scope of any claimed embodiment.

Figure 2A:
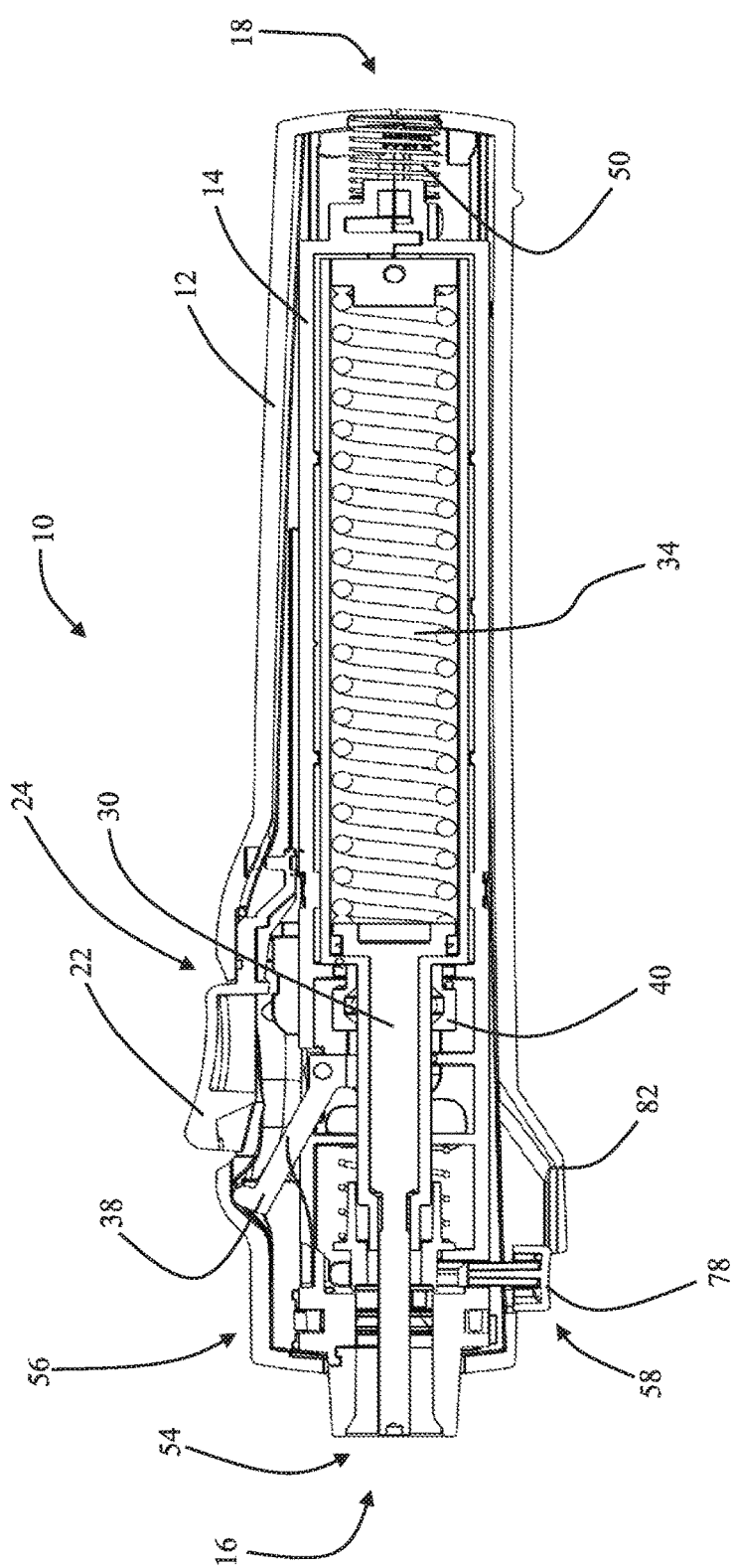
FIG. 2A is a side cross-sectional view of the needle-free injection device of FIG. 1 while the device is positioned in the syringe loading position prior to arming the spring power source for injection and prior to loading a needle-free syringe.
Figure 2B:
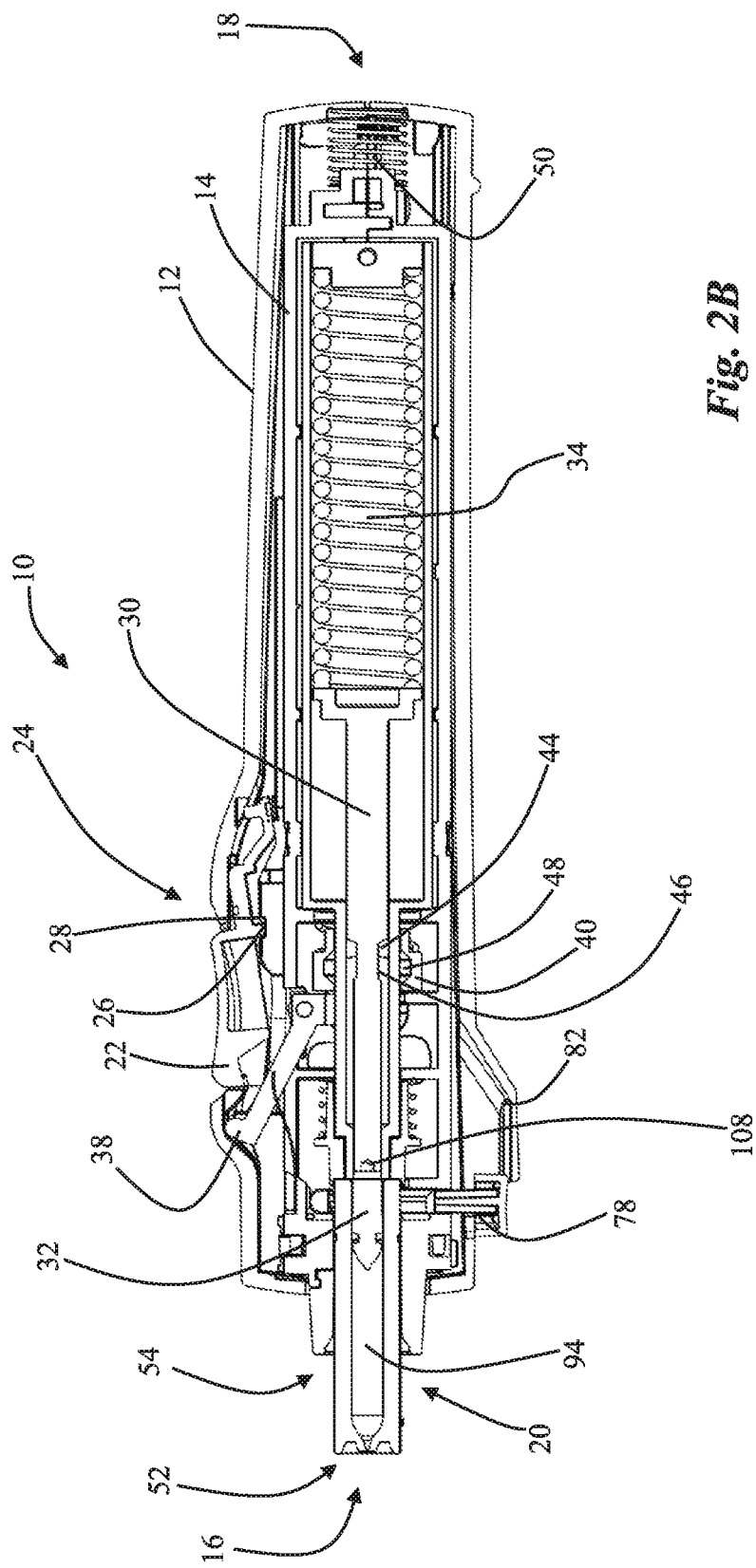
FIG. 2B is a side cross-sectional view of the needle-free injection device of FIG. 1 while the device is positioned in the syringe loading position but after the device has been armed for injection and after a needle-free syringe has been mounted.
Figure 2C:
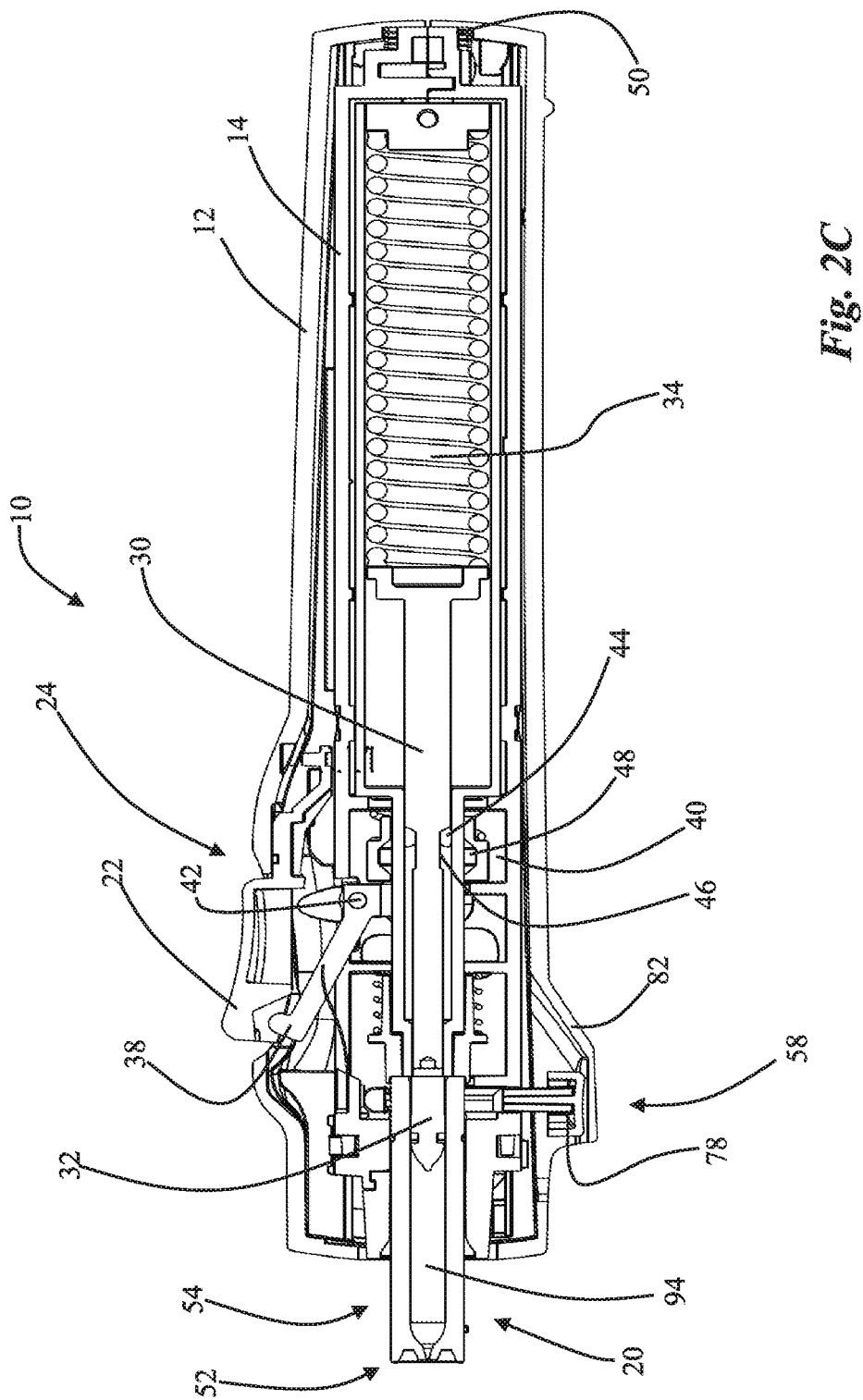
FIG. 2C is a side cross-sectional view of the needle-free injection device of FIG. 1 while the device is positioned in the firing position immediately prior to an injection.

As shown in FIGS. 2A-2C, the inner housing 14 is movable within the outer housing 12 between a syringe loading position and a firing position. In particular, FIG. 2A shows the device 10 in a storage configuration prior to or after use. FIG. 2B shows the device 10 with a needle free syringe 20 installed. Both FIGS. 2A and 2B illustrate a needle-free injection device 10 with the inner housing 14 positioned in what is defined herein as the syringe loading position. In FIGS. 2A and 2B it may be noted that the inner housing 14 is positioned toward the leading end 16 of the device with respect to the outer housing 12. This configuration is specifically the syringe loading position of this particular embodiment. More generally, a syringe loading position is defined for any device as a configuration between inner and outer housings where syringe loading or syringe ejection is enabled and injection is substantially prohibited.

In addition, for any configuration of device, a firing position is defined as a configuration between inner and outer housings where injection is enabled. As discussed in detail below the safety and efficiency of a device may be enhanced by providing distinct syringe loading and firing configurations. FIG. 2C illustrates the needle-free injection device 10 in the firing position, for this embodiment. In particular, FIG. 2C shows the inner housing 14 positioned within the outer housing 12 toward the trailing end of the device. As described in detail below the movement of the inner housing from a syringe loading position to a firing position provides numerous safety and injection reliability advantages. It should be noted that the specific configurations of FIG. 2 are not limiting. As described above, other configurations or relationships between an inner housing movable with respect to an outer housing could define different syringe loading positions or firing positions for an alternative device configuration.

The needle-free injection device 10 also includes an activation button 22 operatively associated with both the outer housing 12 and inner housing 14. As described in detail below, the activation button 22 may be configured to activate various device functions depending upon the positional relationship between the inner housing 14, outer housing 12 and other elements of the needle free injection device 10.

It may be desired in selected embodiments to provide a housing lock 24 which prohibits movement of the inner housing 14 with respect to the outer housing 12. For example, a housing lock 24 may provide safety by prohibiting movement of the inner housing 14 from the syringe loading position to the firing position during a syringe loading procedure. In the embodiment of FIG. 2A-2C, the housing lock 24 may be engaged by depressing the activation button 22 while the device is in the syringe loading position. In particular, as shown in FIG. 2B, the activation button 22 may include an engagement surface 26 which, when the button 22 is depressed, mates with a corresponding recess 28 to prohibit movement of the inner housing 14 toward the trailing end of the device, thus locking the device in the syringe loading position. The inclusion of a housing lock 24 minimizes the risk of inadvertently firing the needle-free injection device 10 during preliminary procedures such as syringe loading.

The needle-free injection device 10 illustrated in FIGS. 1-2 also includes a hammer 30 configured to drive a syringe plunger 32 forward providing for an injection. In the embodiment of FIGS. 1 and 2 the hammer 30 is energetically driven toward the plunger 32 by energy previously stored compressing a main spring 34. Main spring 34 is shown in an un-compressed state in FIG. 2A and compressed in FIG. 2B. It is important to note that the embodiments disclosed and claimed herein are not limited to needle-free injection devices 10 which rely upon a spring for injection power. The elements, components and methods described herein could be implemented in a pneumatic device, an electronically driven device or any other type of needle-free injector. Thus, in alternative embodiments the main spring 34 could be replaced with a compressed gas source, pneumatic chamber, a motor, an electromagnet or other power source.

The device embodiment of FIGS. 1-2 further includes a release mechanism 36 operatively associated with the hammer 30 such that the release mechanism 36 can be activated to initiate the release of energy stored in the main spring 34 to power the hammer 30 and thereby cause an injection. In the particular embodiment illustrated in FIGS. 1-2 the release mechanism 36 includes a lever 38 and ball lock sleeve 40 which cooperate to releases the hammer 30 when the lever is articulated by the activation button 22. Comparison of FIG. 2B with FIG. 2C shows that the lever 38 is intentionally not in mechanical communication with the activation button 22 until such time as the inner housing 14 is moved from the syringe loading position to the firing position. Thus, the activation button 22 cannot fire the device unless the device is in the firing position. Therefore, the single activation button 22 may be depressed to lock the inner housing during loading procedures in the syringe loading position or alternatively depressed to fire the device when the inner housing has been moved to the firing position. The configuration of the housing lock 24 and release mechanism 36 guarantee that the activation button 22 can only perform the appropriate function at the appropriate time based upon the positioning of the inner housing.

The specific embodiment illustrated in FIG. 2 accomplishes firing by the articulation of the lever 38 with the activation button 22 while the inner housing is in the firing position as shown in FIG. 2C. The lever 38 rotates around a pivot 42 and pushes the ball lock mechanism 40 toward the trailing edge of the device. When the ball lock mechanism 40 is moved back a suitable distance, ball bearings 44 are released from a notch 46 in the hammer 30 and forced into channels 48 of the ball lock, thus releasing the hammer 30 to power an injection. It is important to note that any alternative triggering mechanism which is suitable for articulation by the activation button 22 may be used to implement or cause the firing of the device.

The ability of the functional elements of the needle-free injection device 10 to enhance the safety and reliability of an injection in both the syringe loading position and firing position are described in additional detail below. Initially, it may be noted that the device 10 includes a skin tensioning spring 50 positioned between the outside trailing end of the inner housing 14 and the inside trailing end of the outer housing 12. The skin tensioning spring 50 element may be implemented with a compression spring which has a relatively lower spring constant than the main spring 34. Alternatively, other compression elements such as elastomeric rings or wave washers could be used to implement the skin tensioning spring 50. The skin tensioning spring 50 installed as shown in FIGS. 2A-2C will bias the inner housing 14 toward the syringe loading position.

As described above, the activation button 22 may be used to engage a housing lock 24 locking the inner housing 14 into the syringe loading position for syringe loading or other pre-injection tasks. Prior to an injection the housing lock 24 may be released and the nozzle end 52 of a needle-free syringe 20 placed against a patient's skin at the injection site. It is important for both safety and injection consistency that the patient's skin be placed under appropriate tension prior to the needle-free injection. Appropriate skin tension is accomplished in the needle-free injection device 10 as force against the skin by the nozzle end 52 is transferred through the syringe 20 to the inner housing thereby causing the inner housing to move toward the firing position and compressing the skin tensioning spring 50. Thus, as shown by comparing FIGS. 2B and 2C, compression of the skin tensioning spring 50 occurs in conjunction with movement of the inner housing 14 toward the firing position. Furthermore, compression of the skin tensioning spring 50 requires the operator to press the nozzle end 52 of the syringe against the patient's skin with an appropriate force. The operator is holding the outer housing 12 during an injection so the physical act of pressing the nozzle end 52 against the patient's skin with sufficient force causes the configuration of the inner housing 14 with respect to the outer housing 12 to move from the syringe loading position to the firing position. Since the skin tensioning spring resists this movement, appropriate injection site skin tension is tunable for different situations by selecting an appropriately sized skin tensioning spring 50 or providing an adjustable spring pre-load.

As shown in FIG. 2A the needle free injection device 10 will typically be delivered to an end user without a needle-free syringe 20 attached. As described in detail below, a user may fill multiple needle-free syringes 20 with an injectable fluid in advance, possibly at a remote location away from the needle-free injection device 10. Advance preparation of multiple needle free syringes 20 facilitates large inoculation projects for example.

Thus, the needle-free injection device 10 is configured to efficiently and accurately receive, hold and eject a needle-free syringe 20. The installed needle-free syringe 20 may be selected from a supply of prefilled syringes. In addition it may optionally be desirable that a syringe can be mounted and ejected without touching the syringe body with an operator's hands to minimize the risk of syringe contamination or operator injury. Accordingly, the needle-free injection device 10 may include a syringe mount 54, an interlocking structure 56, and an ejection mechanism 58 which separately or together enhance several aspects of the safe use of the device.

For example, as shown in the top cross sectional views of FIGS. 3A-3D the needle-free injection device 10 may include a syringe mount 54 comprising a socket 60 sized to receive a suitable needle-free syringe 20. Pawls 62 or a similar grasping or locking structure may be provided adjacent to the socket and configured to positively grip an appropriate grip surface 64 on a needle-free syringe 20. It may be noted from FIG. 3B which shows a needle-free injection device 10 in the syringe loading position while a syringe is in the process of being loaded that the trailing end of the syringe 20 is received in an ejection sleeve 66 and an ejection spring 68 is compressed. The ejection sleeve 66 and ejection spring 68 facilitate the optional hands free ejection of a syringe as described below.

Figure 3A:
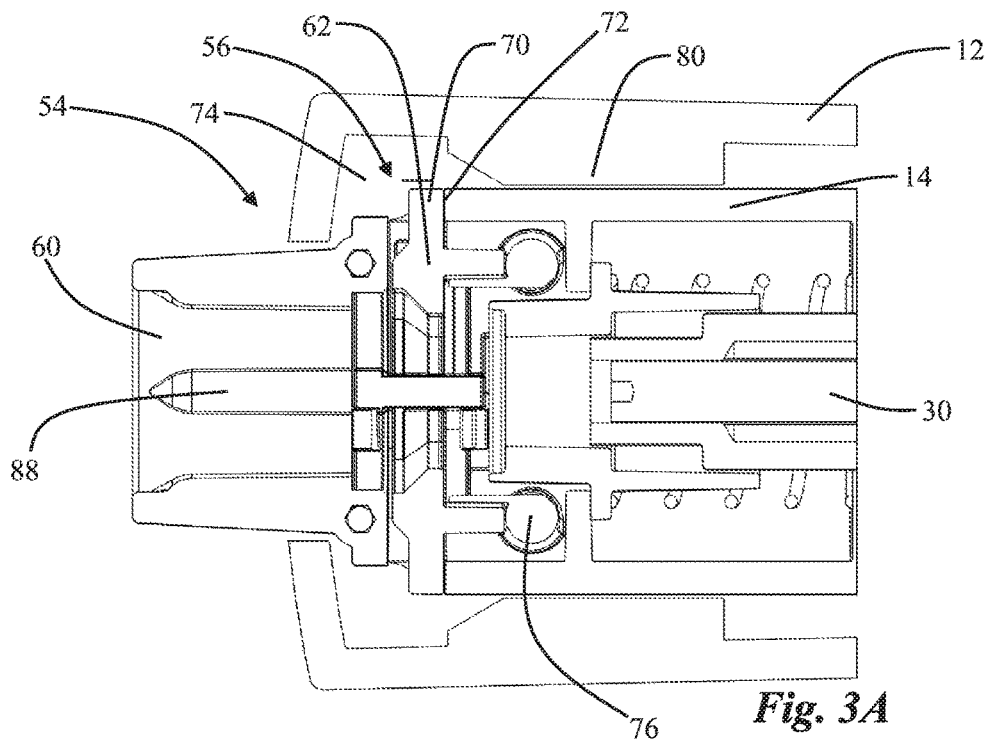
FIG. 3A is a top cross-sectional view of the leading end of the needle-free injection device in the position and configuration illustrated in FIG. 2A.
Figure 3B:
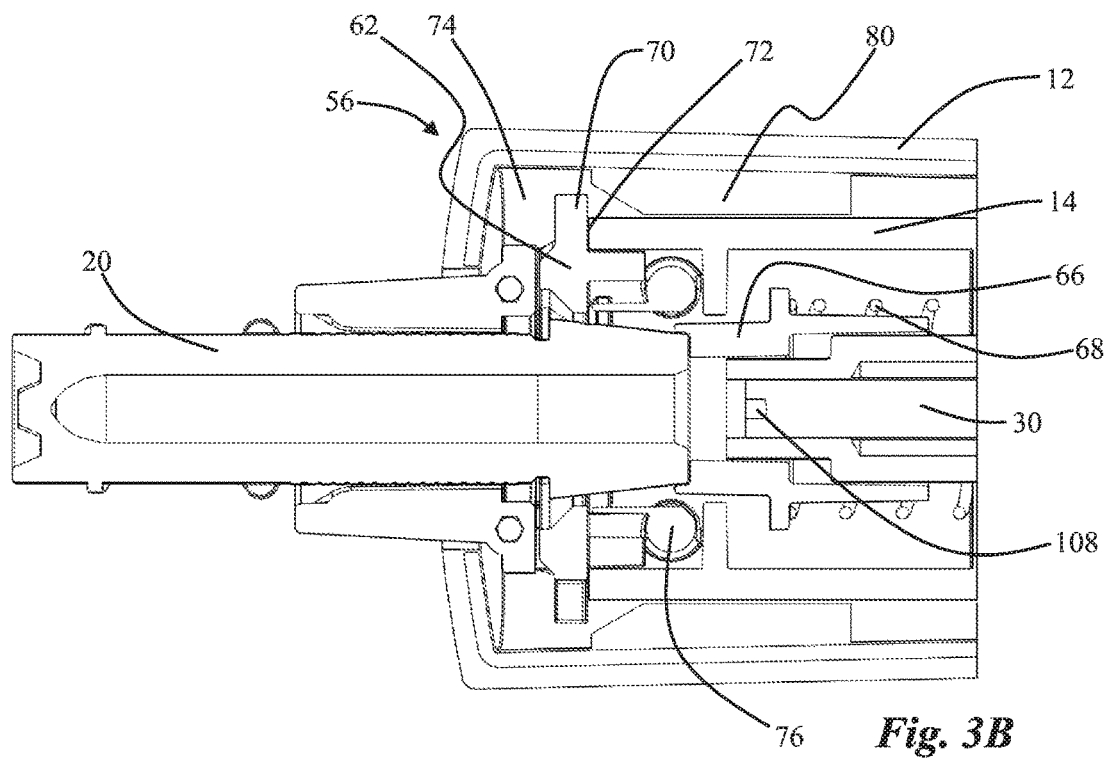
FIG. 3B is a top cross-sectional view of the leading end of the needle-free injection device in the syringe loading position during the process of syringe loading.
Figure 3C:
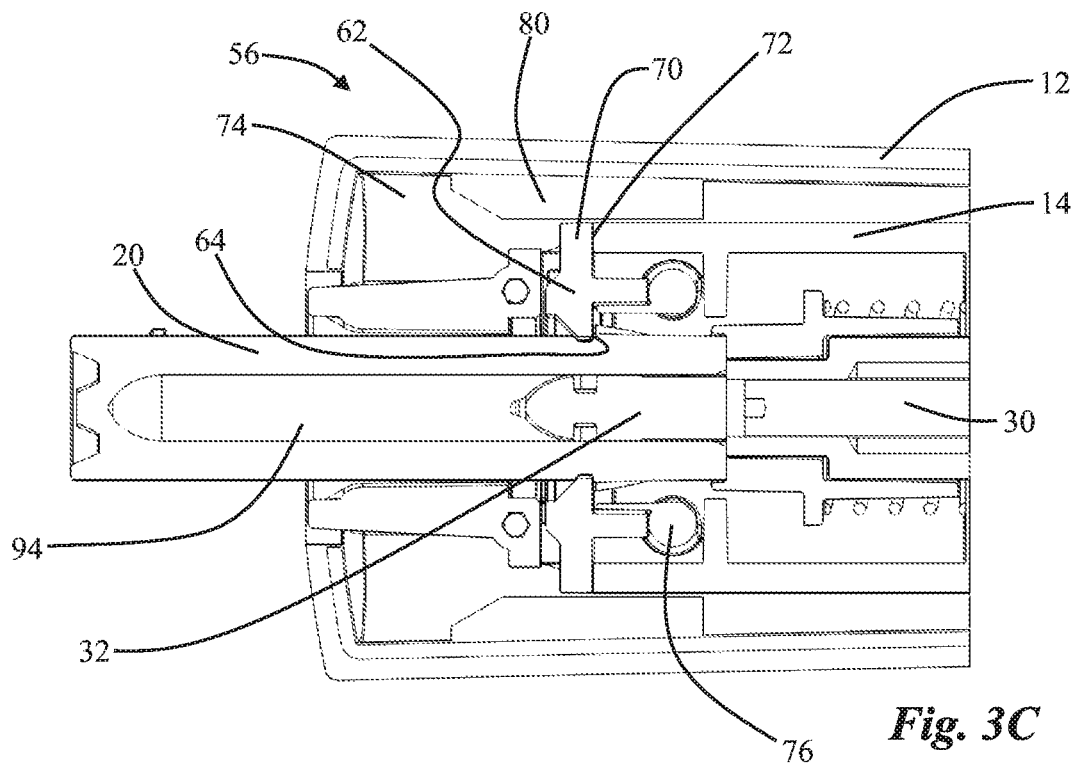
FIG. 3C is a top cross-sectional view of the leading end of the needle-free injection device in the firing position and configuration illustrated in FIG. 2C.

The safe and efficient use of the needle-free injection device 10 may be further enhanced if the device is provided with an interlocking structure 56 which prevents the placement of a needle-free syringe 20 into an engagement with the syringe mount 54 unless the inner housing 14 is in the syringe loading position. Alternatively, or in addition to this functionality, the interlocking structure 56 may prevent removal of a needle-free syringe 20 unless the inner housing 14 is also in the syringe loading position. One representative and non-limiting example of an interlocking structure 56 may be viewed in FIGS. 3A-3D and includes at least one tab 70 on an outer perimeter surface of a pawl 62. The tab 70 corresponds with an opening 72 defined by the inner housing 14 and a corresponding open area 74 within the outer housing 12 such that the tab 70 may extend through the opening 72 into the area 74 when the pawls 62 rotate outward and extend over the trailing end of a suitably shaped needle-free syringe 20. FIG. 3B in particular shows the tab 70 extending through the opening 72 and into the area 74 as a needle-free syringe 20 is in the process of being mounted.

Figure 3D:
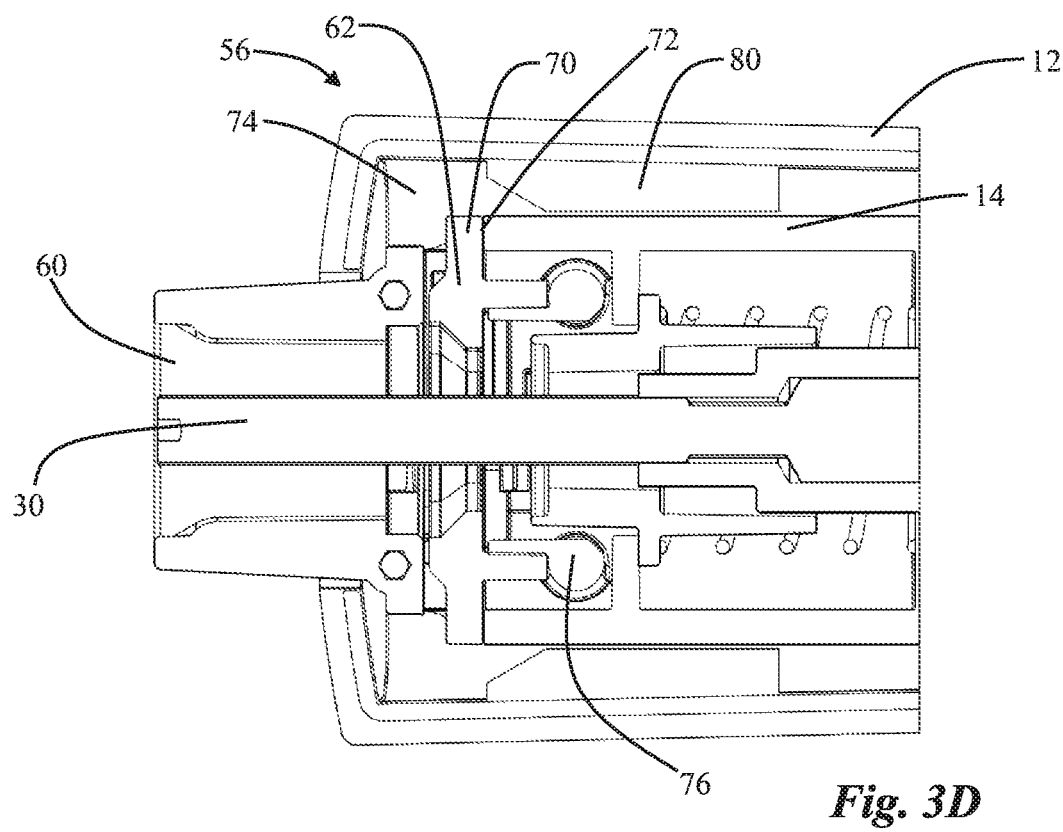
FIG. 3D is a top cross-sectional view of the leading end of the needle-free injection device in the syringe loading position during the ejection of a used syringe.

In addition, as shown in FIG. 3D the tab 70 may extend through the opening 72 into the area 74 when the pawls 62 rotate outward as an inner release mechanism 76 is articulated by an eject button 78. Several safety and efficiency attributes are provided by the interlocking structure 56 because the tab 70 will only correspond with the open area 74 within the outer housing 12 when the inner housing 14 is in the syringe loading position. Any possibility that the tab 70 might extend beyond the inner housing when the inner housing is positioned away from the syringe loading position is prohibited by providing the outer housing 12 with one or more abutment surfaces 80 which prevent a tab 70 from extending beyond the outer surface of the inner housing 14 if the inner housing 14 has moved to or toward the firing position. See for example FIG. 3C which is a top plan cross section view of the device in the firing position. Thus, the interface between tab 70 and abutment surface 80 prevents inadvertent ejection of a syringe in either the firing position or in an intermediate position between the syringe loading position and the firing position.

Furthermore, an improperly loaded syringe will prevent the pawls 62 from rotating into secure contact with the grip surface 64 of a needle-free syringe 20. Thus, an improperly loaded syringe will cause tab 70 to extend into the open area 74 within the outer housing 12. Accordingly, a device with an improperly loaded syringe cannot have the inner housing moved into the firing position because tab 70 will interfere with abutment surface 80, preventing movement of the inner housing toward the trailing end of the device.

Referring back to FIG. 2C which shows a loaded needle-free injection device 10 in the firing position, it may be noted that supplemental safety may be provided by including an extension 82 on the outer housing that fully or partially shields the eject button 78 when the inner housing 14 is moved from the syringe loading position toward the firing position.

The syringe ejection spring 68 may be selected to provide enough force to completely eject a spent needle-free syringe 20 from the device 10 without requiring a user to touch the needle-free syringe. Alternatively, a device can be configured to only partially release a syringe which may then be manually removed.

Figure 4:
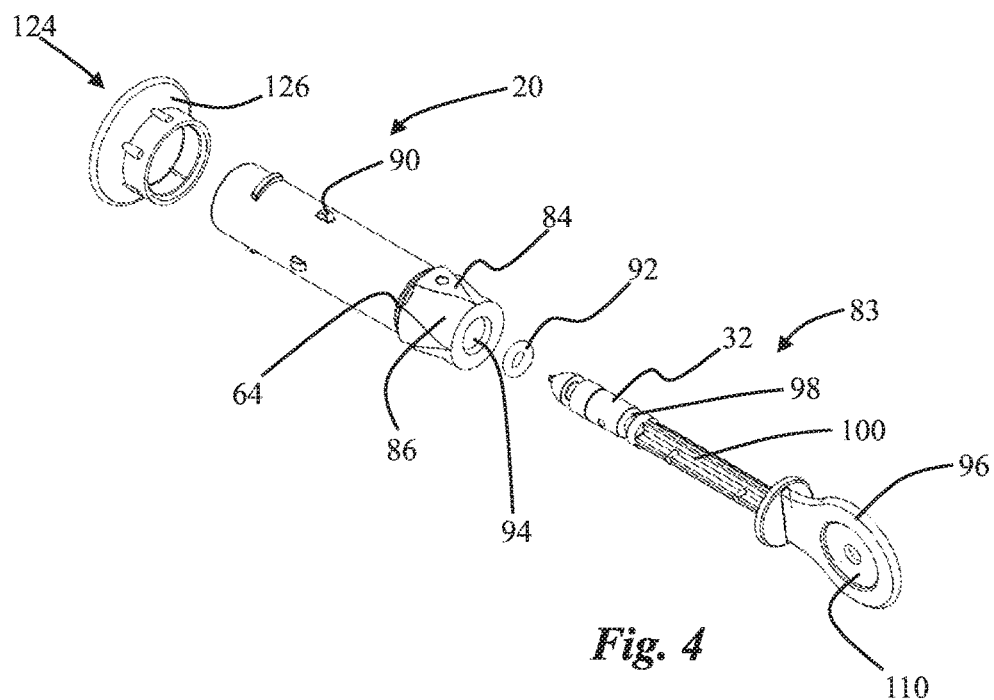
FIG. 4 is an exploded perspective view of a needle-free syringe and plunger system.

FIG. 4 is an exploded perspective view of a needle-free syringe 20 and syringe plunger system 83 showing certain enhancements. In particular, the needle-free syringe 20 may include at least two raised surfaces 84 defining at least one orientation channel 86 on the body of the needle-free syringe, typically at the trailing end. The orientation channel 86 is sized and configured to engage with corresponding syringe orientation guides 88 which are best viewed in FIG. 3A in association with the interior surface of the syringe mount socket 60. Thus, a user may install a needle-free syringe 20 by sliding one or more orientation channels 86 over corresponding orientation guides 88 until the pawls 62 engage with the syringe grip surface 64. Therefore, a syringe may be installed and locked for use without requiring the syringe body to be twisted as is necessary with conventional bayonet or screw type syringe mounts. Referring back to FIG. 4, the needle-free syringe 20 may also include visual indicia 90 which are illustrated as small raised portions but which could be implemented with any visually observable marker. In use the visual indicia are placed in a visually identifiable position relative to or concealed by the leading end of the socket 60 thereby providing visual confirmation that a syringe 20 is properly installed.

Figure 5:
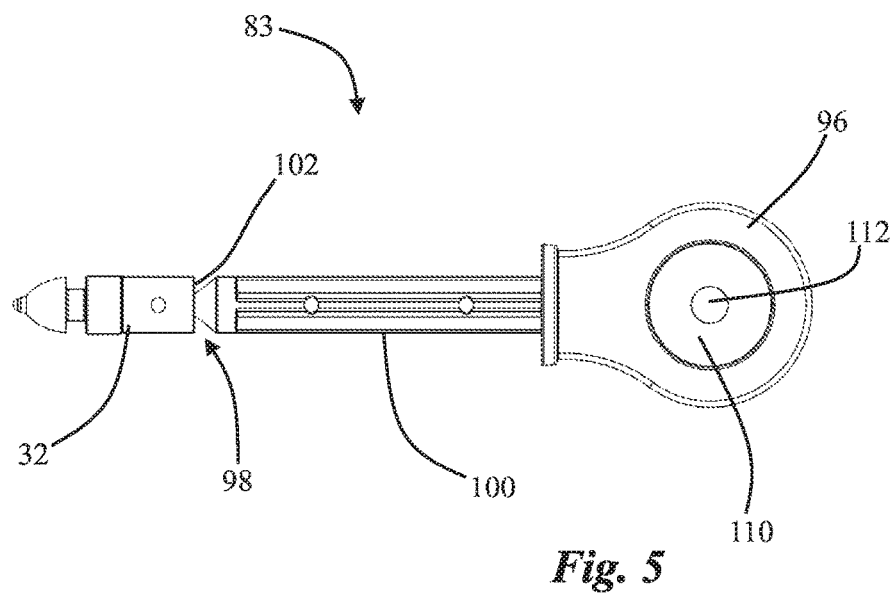
FIG. 5 is a front elevation view of a plunger and handle system.

As noted above, it may be most convenient to remotely prepare multiple needle-free syringes 20 for use with the needle-free injection device 10. For example, one operator could be loading needle-free syringes with an injectable fluid while another operator installs the needle-free syringes into the device and performs injections. Remote filling to a proper pre-determined dosage is facilitated by providing a plunger system 83 which includes a plunger body 32 and a seal 92 sized to fit in fluid-tight engagement with the interior chamber of the syringe, thereby defining a fluid receiving dosage space 94 within a needle-free syringe 20. As shown in FIG. 5, the plunger system 83 also may include a handle 96. The handle 96 may be conveniently separated from the plunger body 32 at a break line 98 defined in a separable shaft 100 between the plunger body 32 and handle 96. In use the handle 96 and separable shaft 100 are typically broken away from the plunger body at the break line 98 after the syringe is filled, but before it is loaded into a device 10. Upon removal of the handle 96 and separable shaft 100, the trailing end of the plunger body 32 defines a hammer surface 102 which in use engages with the hammer 30 during an injection.

As shown in FIGS. 2B and 6A-6B, the interior portion of the syringe 20 defines a dosage space 94 within the interior walls of the syringe between the nozzle 104 and the plunger seal 92. This dosage space 94 may be sized and configured to have a pre-selected injectable fluid dosage volume when the plunger body 32 is positioned within the syringe such that the hammer surface 102 is placed in a pre-defined spatial relationship with a dose setting surface 106 on the trailing edge of the syringe, substantially opposite the nozzle 104. For example, the dosage space 94 may be sized to have a specific volume, for example 0.5 ml, when the hammer surface 102 is coplanar with the dose setting surface 106. This particular configuration is illustrated in FIGS. 2B and 2C.

As shown in FIG. 2B, the hammer 30 may be used to automatically position the plunger body 32 such that the hammer surface 102 and dose setting surface 106 are coplanar. It may also be noted that the leading edge of the hammer 30 includes a recess 108 which provides clearance for any extension or nub remaining beyond the hammer surface when the separable shaft 100 is removed from the plunger body 32 at the break line 98.

Proper dose setting may also be accomplished in the absence of the needle-free injection device 10 by using the plunger positioning surface 110 associated with the handle 96 to manually position the hammer surface 102 to be coplanar with the dose setting surface 106. The plunger positioning surface 110 may, as shown in FIG. 5, include a hole 112 which provides clearance for any extension or nub formed in the hammer surface 102 upon separation of the plunger body 32 from the handle 96 at the break line 98. Thus, during a remote filling operation, a user may insert the plunger body 32 and attached handle 96 fully into a needle-free syringe 20 such that the leading end of the plunger body 32 is in contact with the interior surface of the nozzle 104. The nozzle 104 may be placed in fluid communication with a supply of injectable material. The handle 96 may be then be used to withdraw the plunger body 32 to a point where the hammer surface 102 extends beyond the dose setting surface 106 of the syringe, thereby slightly over-filling the syringe. The handle 96 and separable shaft 100 may then be removed at the break line 98 and the hammer surface 102 and dose setting surface 106 made to be coplanar (thus precisely setting the selected dosage) by pressing upon the hammer surface 102 with the plunger positioning surface 110 of the handle. The foregoing operation may be performed while the nozzle 104 is continuously maintained in sterile fluid communication with an injectable substance supply, thus minimizing waste.

The remote filling of a needle-free syringe 20 may be facilitated by providing a filling adapter 114 as shown in FIGS. 7A-7B. The filling adapter 114 may include a male or female conical attachment surface 116 as illustrated in FIG. 7A. This conical attachment surface 116 is configured to mate with a corresponding male or female conical surface 118 positioned at the nozzle end 52 of a needle-free syringe 20 as shown in FIG. 6B. Thus, the corresponding male and female conical surfaces 116, 118 form a fluid tight seal upon attachment of the filling adapter to the nozzle end of a syringe without the use of any separate compliant sealing member, an o-ring for example.

It may further be noted from FIG. 7B that the ergonomic use of the filling adapter 114 may be enhanced by providing stability wings 120 which provide a safe grip surface and substantially protect a filling needle 122 from contamination.

Returning to FIG. 4 it may be noted that the needle-free syringe 20 may be provided with a cap 124 sized to engage the nozzle end 52 of the syringe body. The cap 124 may be provided with an annular flange 126 at the closed end of the cap providing a stand surface with a diameter greater than the diameter of the open end of the cap body. In use, the stand surface may be employed to stand an array of filled needle-free syringes 20 upright in a ready position for engagement with a needle-free injection device 10. Thus, if desired a needle-free syringe 20 may be loaded and ejected in an efficient hands free manner.

Alternative embodiments include methods of operating and filling a needle-free injector as described above. For example, one method includes providing a needle-free injection device 10 according to any one of the alternative embodiments described herein. The method further includes activating the activation button 22 to lock the inner housing 14 in the syringe loading position and subsequently loading a needle-free syringe 20 into the injector. An operator may then release the activation button 22 and move the inner housing 14 to the firing position by pressing the nozzle end 52 of the needle-free syringe 20 against the injection site with sufficient force. The injection may then be triggered by activating the activation button 22 when the inner housing is fully in the firing position. Optionally, the method may include steps of loading and ejecting a needle free syringe 20 from the device. Loading and ejection may occur without touching the syringe at any time.

Another alternative embodiment is a method of filling a needle-free syringe 20 including providing a syringe having a nozzle 104 at one end and a dose setting surface 106 substantially opposite the nozzle 104. The method further includes providing a plunger body 32 in sealed engagement with an inner surface of the syringe 20 where the plunger body 32 further comprises a hammer surface 102. The filling method further comprises positioning the hammer surface 102 to be substantially coplanar with the dose setting surface 106.

An alternative method of filling a needle-free syringe may include providing a filling adapter 114 with a filling needle 122 in sealed fluid communication with the nozzle 104 of the syringe body. A plunger system 83 including a handle 96 as described above may be placed into engagement with the syringe 20. The plunger body 32 may then be moved forward to the nozzle end of the syringe body. The septum of storage vial of injectable fluid may be pierced with the filling needle 122. The plunger system 83 is then withdrawn by the handle to a position where the break line 98 is beyond the dose setting surface 106. The handle 96 is then removed from the plunger body 32 by separating the shaft 100 at the break line 98. Next, the plunger body 32 may be moved toward the nozzle 104 by applying force against the hammer surface 102 with a plunger positioning surface 110 causing the hammer surface 102 and dose setting surface 106 to become coplanar. Alternatively, the dose may be set by using a surface within the device, for example the leading edge of the hammer 30 to cause the hammer surface to become coplanar with the dose setting surface. Throughout the dose setting operation the filling adapter and needle-free syringe remain in direct fluid communication with the storage vial of injectable fluid, thereby allowing the precise setting of an injection dosage without the waste of any substantial amount of injectable fluid.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the embodiments described herein have been particularly shown and described with reference to a number of possible variations, it would be understood by those skilled in the art that changes in the form and details may be made to various components or elements without departing from the spirit and scope of the embodiments and that the various embodiments disclosed herein are not intended to act as limitations on the scope of the claims. All references cited herein are incorporated in their entirety by reference.

What is claimed is:

1. A method of operating a needle-free injector comprising:
 providing a needle-free injector comprising an outer housing, an inner housing moveable within the outer housing between a syringe loading position and a firing position, an activation button operatively associated with the inner and outer housing, and a housing lock engaged by the activation button;
 activating the activation button when the inner housing is in the syringe loading position to lock the inner housing in the syringe loading position; and
 loading a needle-free syringe into the needle-free injector.

2. The method of claim 1 further comprising:
 releasing the activation button while the inner housing is in the syringe loading position;
 moving the inner housing to the firing position; and
 triggering the delivery of a fluid injection by activating the activation button when the inner housing is in the firing position.

3. The method of claim 2 further comprising:
 providing the needle-free injector with an eject button which is separate from the activation button; and
 ejecting the needle-free syringe from the needle-free injector by activating the eject button.

4. The method of claim 3 further comprising preventing activation of the eject button when the inner housing is moved from the syringe loading position toward the firing position.

5. The method of claim 3 further comprising:
 providing the needle-free injector with an extension on the outer housing that at least partially shields the eject button when the inner housing is moved from the syringe loading position toward the firing position; and
 preventing activation of the eject button with the extension, when the inner housing is moved from the syringe loading position toward the firing position.

6. The method of claim 3 further comprising providing the needle-free injector with a syringe eject spring providing sufficient force to completely eject a needle free syringe away from any contact with the needle-free injector upon activation of the eject button.

7. The method of claim 1 further comprising preventing the loading of the needle-free syringe into engagement with a syringe mount at one end of the inner housing, unless the inner housing is in the syringe loading position.

8. The method of claim 1 further comprising causing the inner housing to move from the syringe loading position toward the firing position by applying force to a nozzle end of the needle-free syringe.

9. The method of claim 1 further comprising preventing the removal of the needle-free syringe from engagement with a syringe mount at one end of the inner housing, unless the inner housing is in the syringe loading position.

10. The method of claim 1 further comprising preventing the inner housing from being moved from the syringe loading position to the firing position if the syringe is not properly loaded in a syringe mount at one end of the inner housing.

11. A method of operating a needle-free injector comprising:
 providing a needle-free injector comprising an outer housing, an inner housing moveable within the outer housing between a syringe loading position and a firing position, and a syringe mount; and
 loading a needle-free syringe into the syringe mount, wherein the syringe mount prevents the placement of the needle-free syringe into engagement with the syringe mount unless the inner housing is in the syringe loading position.

12. The method of claim 11 further comprising causing the inner housing to move from the syringe loading position toward the firing position by applying force to a nozzle end of the needle-free syringe.

13. The method of claim 11 further comprising preventing the removal of the needle-free syringe from engagement with the syringe mount, unless the inner housing is in the syringe loading position.

14. The method of claim 11 further comprising preventing the inner housing from being moved from the syringe loading position to the firing position if the syringe is not properly loaded in the syringe mount.

15. A method of operating a needle-free injector comprising:

providing a needle-free injector comprising an outer housing, an inner housing moveable within the outer housing between a syringe loading position and a firing position, a syringe mount providing for the attachment of a need free syringe to one end of the inner housing, and an eject button;

loading a needle-free syringe into the syringe mount; and ejecting the needle-free syringe from the syringe mount by activating the eject button.

16. The method of claim 15 further comprising preventing activation of the eject button when the inner housing is moved from the syringe loading position toward the firing position.

17. The method of claim 15 further comprising:

providing the needle-free injector with an extension on the outer housing that at least partially shields the eject button when the inner housing is moved from the syringe loading position toward the firing position; and preventing activation of the eject button with the extension, when the inner housing is moved from the syringe loading position toward the firing position.

18. The method of claim 15 further comprising providing the needle-free injector with a syringe eject spring providing sufficient force to completely eject a needle free syringe away from any contact with the needle-free injector upon activation of the eject button.

* * * * *